(12) United States Patent
Jönsson et al.

(10) Patent No.: US 7,771,380 B2
(45) Date of Patent: Aug. 10, 2010

(54) PRESSURE SENSING

(75) Inventors: Lennart Jönsson, Furrulund (SE); Johan Drott, Lund (SE); Thomas Hertz, Lund (SE)

(73) Assignee: Gambro Lundia AB, Lund (SE)

( * ) Notice: Subject to any disclaimer, the term of this patent is extended or adjusted under 35 U.S.C. 154(b) by 549 days.

(21) Appl. No.: 10/589,353

(22) PCT Filed: Feb. 11, 2005

(86) PCT No.: PCT/SE2005/000184

§ 371 (c)(1),
(2), (4) Date: Aug. 11, 2006

(87) PCT Pub. No.: WO2005/077262

PCT Pub. Date: Aug. 25, 2005

(65) Prior Publication Data

US 2007/0179433 A1    Aug. 2, 2007

Related U.S. Application Data

(60) Provisional application No. 60/544,205, filed on Feb. 12, 2004.

(30) Foreign Application Priority Data

Feb. 12, 2004   (SE) .................................... 0400330

(51) Int. Cl.
*A61M 37/00* (2006.01)
*C02F 1/00* (2006.01)
*G01L 7/10* (2006.01)

(52) U.S. Cl. .................... 604/5.01; 604/5.04; 604/6.01; 210/645; 210/741; 73/729.2

(58) Field of Classification Search ................ 604/5.01, 604/6.01, 5.04; 210/245, 646, 739, 741; 600/488; 73/729.2, 861, 44, 722, 753
See application file for complete search history.

(56) References Cited

U.S. PATENT DOCUMENTS

| | | | | |
|---|---|---|---|---|
| 5,756,900 A | * | 5/1998 | Arie et al. ..................... 73/756 |
| 5,807,258 A | * | 9/1998 | Cimochowski et al. ..... 600/454 |
| 5,873,840 A | * | 2/1999 | Neff ........................... 600/561 |
| 6,272,930 B1 | * | 8/2001 | Crozafon et al. ........... 73/729.2 |
| 6,484,586 B1 | * | 11/2002 | Dutoit et al. .................. 73/722 |
| 7,059,195 B1 | | 6/2006 | Liu |
| 2002/0007137 A1 | | 1/2002 | Utterberg et al. |

(Continued)

FOREIGN PATENT DOCUMENTS

DE        201 13 789 U1    6/2002

(Continued)

OTHER PUBLICATIONS

International Search Report for International Application No. PCT/SE2005/000184, dated May 17, 2005.

*Primary Examiner*—Leslie R Deak
(74) *Attorney, Agent, or Firm*—Finnegan, Henderson, Farabow, Garrett & Dunner, L.L.P.

(57) ABSTRACT

A biological fluid device (703) comprises a pressure sensor (702), which is arranged on the device. The pressure sensor comprises a compressible container, the compression of which is indicative of the pressure, and is capable of wireless communication.

38 Claims, 6 Drawing Sheets

U.S. PATENT DOCUMENTS

| | | |
|---|---|---|
| 2002/0115920 A1 | 8/2002 | Rich et al. |
| 2004/0082867 A1* | 4/2004 | Esch et al. .................. 600/488 |
| 2006/0144155 A1 | 7/2006 | Liu |

FOREIGN PATENT DOCUMENTS

| | | |
|---|---|---|
| DE | 201 21 388 U1 | 10/2002 |
| DE | 201 21 938 U1 | 10/2003 |
| WO | WO 00/72747 A1 | 12/2000 |
| WO | WO 02/22187 A2 | 3/2002 |

* cited by examiner

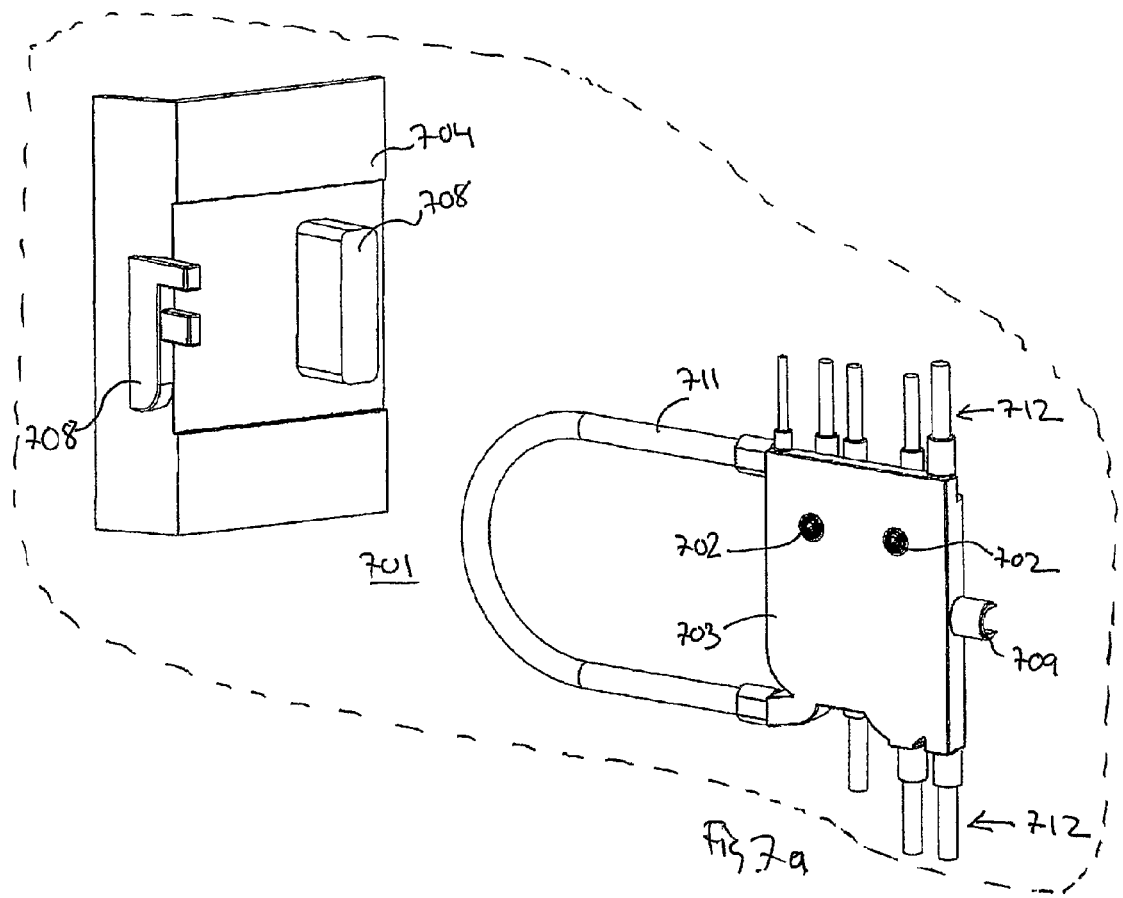

PRESSURE SENSING

CROSS-REFERENCE TO RELATED APPLICATIONS

This application is a national stage filing under 35 U.S.C. §371 of International Application No. PCT/SE2005/000184, filed on Feb. 11, 2005. This application also claims the benefit of priority to Swedish Patent Application No. 0400330-7 filed on Feb. 12, 2004, and to U.S. Provisional Application No. 60/544,205 filed on Feb. 12, 2004, all of which are incorporated herein by reference.

TECHNICAL FIELD

The present invention relates to management of fluids used in a medical procedure and more specifically to pressure sensing in a biological fluid.

BACKGROUND

There are a number of procedures in which biological fluids such as blood, blood components as well as mixtures of blood or blood components with other fluids as well as any other liquid comprising biological cells, are managed. Examples of such procedures include treatments where blood is taken out in an extracorporeal blood circuit. Such treatments involve, for example, hemodialysis, hemofiltration, hemodiafiltration, plasmapheresis, blood component separation, blood oxygenation, etc. Normally, blood is removed from a blood vessel at a blood access and returned to the same blood vessel. During these procedures it is often desirable and also important to monitor the pressure in the biological fluid system.

US patent application 20020007137 describes a prior art dialysis pressure sensing system wherein the pressure in an extracorporeal blood circuit is measured with an ordinary pressure transducer.

Typically, when performing pressure sensing using arrangements according to prior art, the extracorporeal blood circuit is connected to a patient and a dialysis machine. The pressure sensor is located within the dialysis machine and operably and structurally connected to the extracorporeal blood circuit.

Even though the extracorporeal blood circuit typically is in the form of a disposable arrangement there is a risk of cross contamination between patients. Between the pressure sensor in the dialysis machine and the blood in the disposable extracorporeal circuit is arranged an air column in a connector line/column. The air column exerts a backpressure on the blood, thereby preventing blood from getting in contact with the pressure sensor/-machine. The dialysis machine normally comprises pumps of roller type creating a pulsating flow of blood in such a way that blood is penetrating into the connector line to some extent. In case the blood flow is blocked there is a potential risk that the backpressure exerted on the blood by the air column in the connector line is overcome and that blood reach a protective filter, protecting the pressure sensor. In such a case, cross contamination could occur if this situation reoccurs with another patient connected to the machine and the machine has not been cleaned properly. Also there is a potential risk that bacteria could grow in blood residuals at the protective filter.

Another problem is that of leakage, which may occur due to operator mistakes during set-up of the system. Needless to say, leakage could be of danger to an operator of the system in case contaminated blood is present in the system. Leakage may also lead to erroneous or less accurate pressure measurements.

International patent application with publication number WO 02/22187 discloses a blood pump having a disposable blood passage cartridge with integrated pressure sensors. Signal wires convey information from pressure transducers to a controller.

Hence, electrical contact problems may occur due to presence of spillage (or contamination) of fluids such as blood as well as contamination of particles such as salt crystals and burrs. Moreover electric connector means imply that there exist edges, indentations, protrusions etc. in the vicinity of means for transporting fluids, which typically enhances the risk of spillage (or contamination) of fluids as well as particles collecting in the area of the connector means. Needless to say, electrical connectors open to touch by operator, may also constitute an added risk of an operator being subject to electric shock.

Moreover, electric wiring and connectors that are needed for transmission of pressure information from pressure sensors according to prior art are unnecessarily complicated and adds to the risk of mistakes during use.

Thus, there is a general problem of how to provide a disposable fluid arrangement which is electrically safe, avoids risks relating to accumulation of spillage (or contamination) of fluids as well as particles, is easy to set-up, avoid leakage and which reduces the risk of cross contamination between patients and/or operators of the system.

SUMMARY OF THE INVENTION

An object of the present invention is to provide a system capable of overcoming problems related to prior art systems.

The object of the present invention is achieved in different aspects by way of a device, a use of a device, a system, a use of a system and a method according to the appended claims.

An inventive device for transporting biological fluid in at least a part of an extracorporeal circuit, where at least part of the extracorporeal circuit is disposable and comprises at least one pressure sensor configured to be in fluid communication with the biological fluid during use, is characterized in that the at least one pressure sensor is configured for sensing a difference between a pressure of the biological fluid and a reference pressure and comprises an electric circuit that is configured to be energized by an applied alternating first electromagnetic field and configured to communicate information indicative of a pressure from the pressure sensor via a second alternating electromagnetic field.

In an embodiment, the first and second alternating electromagnetic fields are one and the same electromagnetic field and also in an embodiment, the first and second alternating electromagnetic fields are in the radio frequency range.

In an embodiment, the sensor comprises a compressible container, the compression or expansion of which is indicative of the pressure. Preferably, the container is open, i.e. configured with an opening or passage etc., to introduce atmospheric pressure into the container.

According to an embodiment of the present invention the pressure sensor may include components in the form of a capacitance and/or an inductance, of which components at least one is a variable component which varies with the relative compression and/or expansion of the container, said capacitance and/or inductance being part of a resonance circuit.

By having such a sensor it is possible to measure, in a wireless manner, the magnitude of the variable component by measuring the resonance frequency. This is advantageous in that it avoids the drawbacks related to prior art devices as discussed above. Thus, either the variable capacitance or the variable inductance is measured. From earlier measurements, i.e. calibration measurements, of the variable components dependence of the pressure the pressure may be determined.

Although it is preferred that the container is open, it is feasible that in some embodiments the compressible container may include a gas such as air at any known pressure, i.e. a reference pressure in a closed container. Thereby the container may have a known fixed pressure therein, so as to have a reference.

The sensor may be tailored to have any predetermined resonance frequency in an unaffected state. This may be used in an identification procedure by way of radio frequency measurements, in order to provide for identifying between different disposables used in different applications, such as dialyser, cassette, bloodline, ultrafilter, tube, connector, container, chamber, fluid bag, blood bag, collection bags, pump segment part of lineset, oxygenator etc.

A system for managing biological fluids according to the invention comprises a device with at least one pressure sensor as discussed above, at least one transmitter configured to transmit an alternating electromagnetic field to the at least one sensor in the device, at least one receiver configured to receive radio frequency information from the device, wherein the received information is indicative of at least one pressure sensed by the device, and a control unit configured to control the transmitter and the receiver. In an embodiment, the at least one sensor is located in close proximity, e.g. 5 to 40 mm, to the at least one transmitter and the at least one receiver.

An advantage of the invention is that, by disposing with the need for structurally connecting a pressure sensor to an extracorporeal blood circuit, thereby minimizing the air-blood interface, risks of cross contamination between patients and/or operators are avoided.

Another advantage is that it is easy to set-up and thereby avoiding risks of leakage, which may be dangerous to an operator of the system.

Yet another advantage of the present invention is that it provides an integrated pressure sensor which is sufficiently inexpensive to allow each device to be disposed of after each use.

The above aspects may be separate or combined in the same embodiment. Embodiments of the present invention will now be described with reference to the accompanying drawings.

BRIEF DESCRIPTION OF THE DRAWINGS

FIGS. 7a and 7b show a system according to the present invention.

DESCRIPTION OF EMBODIMENTS

The invention will be described initially by way of illustration of an extracorporeal blood circuit during the process of dialysis followed by a description of pressure sensors and concluding with a description of a system comprising a blood circuit, pressure sensors, a transmitter and a receiver.

Figure 1:
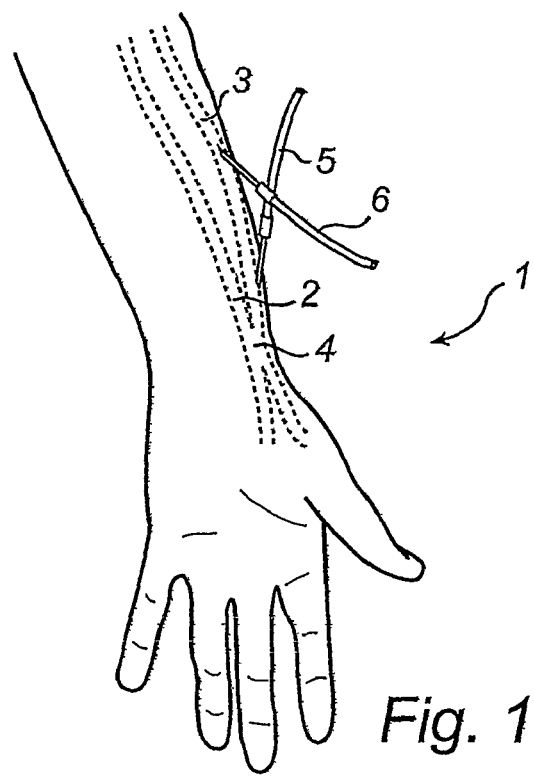
FIG. 1 shows schematically an extracorporeal blood circuit connected to a patient.

FIG. 1 discloses a forearm 1 of a human patient. The forearm comprises an artery 2, in this case the radial artery, and a vein 3, in this case the cephalic vein. Openings are surgically created in the artery 2 and the vein 3 and the openings are connected to form a fistula 4, in which the arterial blood flow is cross-circuited to the vein. Due to the fistula, the blood flow through the artery and vein is increased and the vein forms a thickened area downstream of the connecting openings. When the fistula has matured after a few months the vein is thicker and may be punctured repeatedly. Normally, the thickened vein area is called a fistula. As the skilled person will realize, an artificial vein may also be used.

An arterial needle 5 is placed in the fistula, in the enlarged vein close to the connected openings and a venous needle 6 is placed downstream of the arterial needle, normally at least five centimeters downstream thereof.

Figure 2:
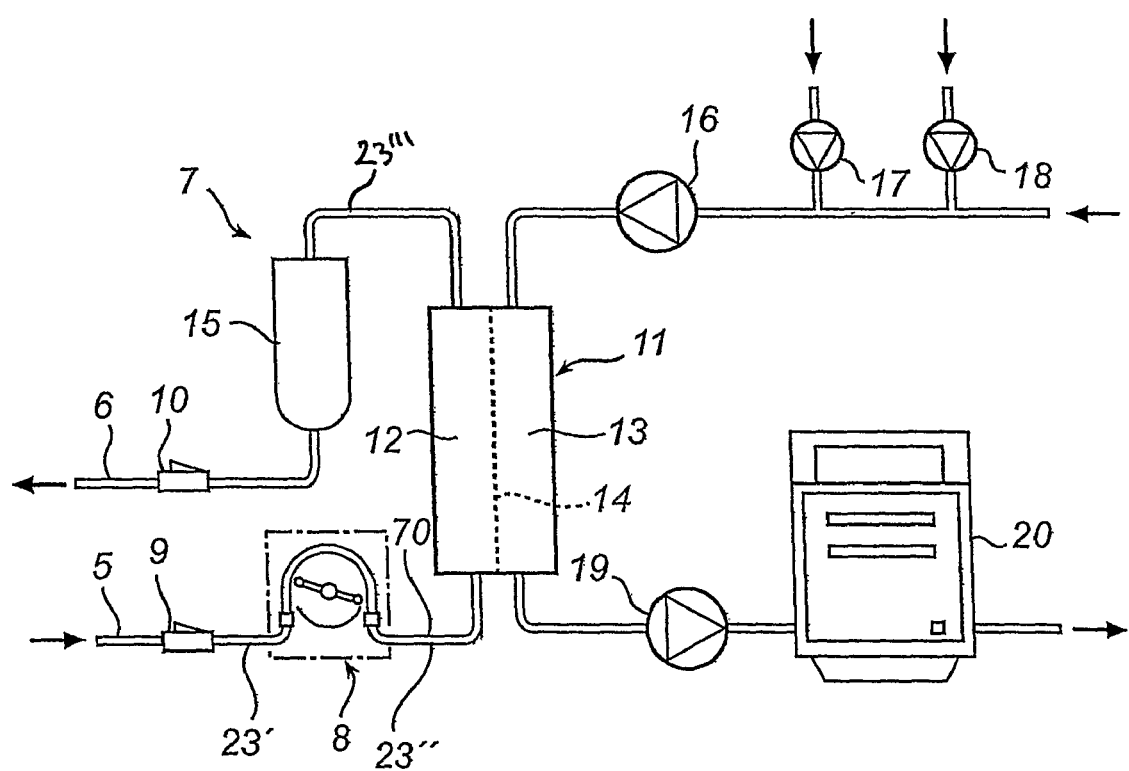
FIG. 2 shows schematically an extracorporeal blood circuit comprising a device according to an embodiment of the present invention.

The needles are connected to a tube system 7 shown in FIG. 2, forming an extracorporeal circuit comprising a blood pump 8, such as may be found in a dialysis circuit. The blood pump transfers blood from the blood vessel, through the arterial needle, the extracorporeal circuit, the venous needle and back into the blood vessel.

The extracorporeal blood circuit 7 shown in FIG. 2 further comprises an arterial clamp 9 and a venous clamp 10 for isolating the patient should an error occur.

Downstream of pump 8 is a dialyzer 11 comprising a blood compartment 12 and a dialysis fluid compartment 13 separated by a semi permeable membrane 14. Further downstream of the dialyzer is a drip chamber 15, separating air from the blood therein.

Blood passes from the arterial needle past the arterial clamp 9 to the blood pump 8. The blood pump drives the blood through the dialyzer 11 and further via the drip chamber 15 and past the venous clamp 10 back to the patient via the venous needle. The drip chamber may comprise air or air bubbles.

The dialysis compartment 13 of the dialyzer 11 is provided with dialysis fluid via a first pump 16, which obtains dialysis fluid from a source of pure water, normally RO-water, and one or several concentrates of ions, metering pumps 17 and 18 being shown for metering such concentrates.

An exchange of substances between the blood and the dialysis fluid takes place in the dialyzer through the semi permeable membrane. Notably, urea is passed from the blood, through the semi permeable membrane and to the dialysis fluid present at the other side of the membrane. The exchange may take place by diffusion under the influence of a concentration gradient, so called hemodialysis, and/or by convection due to a flow of liquid from the blood to the dialysis fluid, so called ultra-filtration, which is an important feature of hemodia-filtration or hemofiltration.

Figure 3:
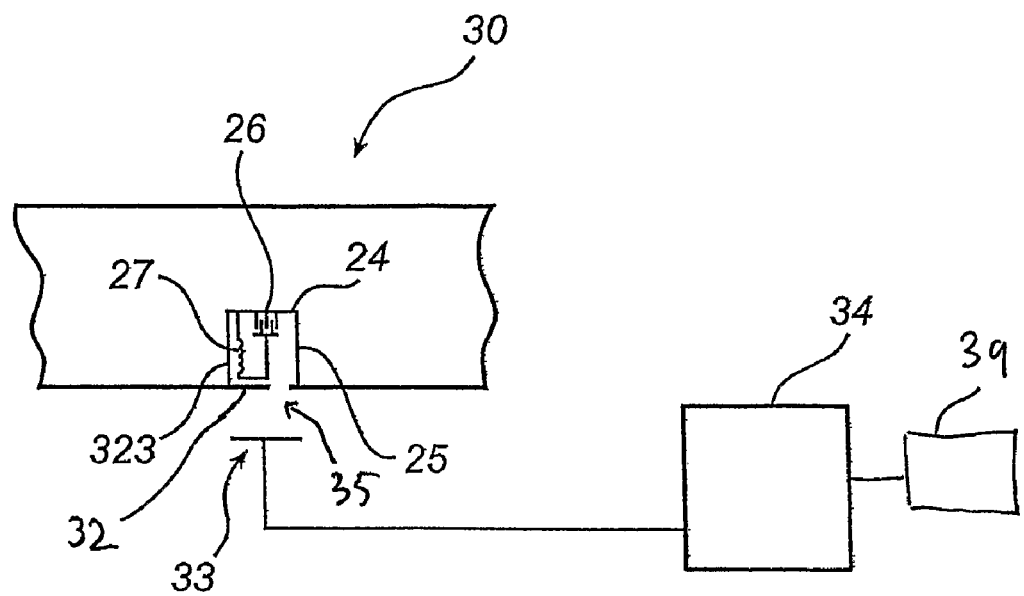
FIG. 3 shows schematically a part of an extracorporeal blood circuit comprising a device with a sensor according to an embodiment of the present invention.

FIG. 3 shows schematically a section of a part of a blood circuit 30 with a pressure sensor 323 according to the present invention. The sensor 323 may be attached inside a tubing line such as line 70 in FIG. 2 after the pump 8 leading to the dialyser, as indicated by reference numeral 23" in FIG. 2. Alternatively the sensor 323 may be arranged in a tubing line 70 before the pump 8, as indicated by reference numeral 23' in FIG. 2. As further alternatives the sensor 23 may be arranged after the dialyzer at reference numeral 23''' or in a drip chamber such as drip chamber 15 in FIG. 2.

Figure 4:
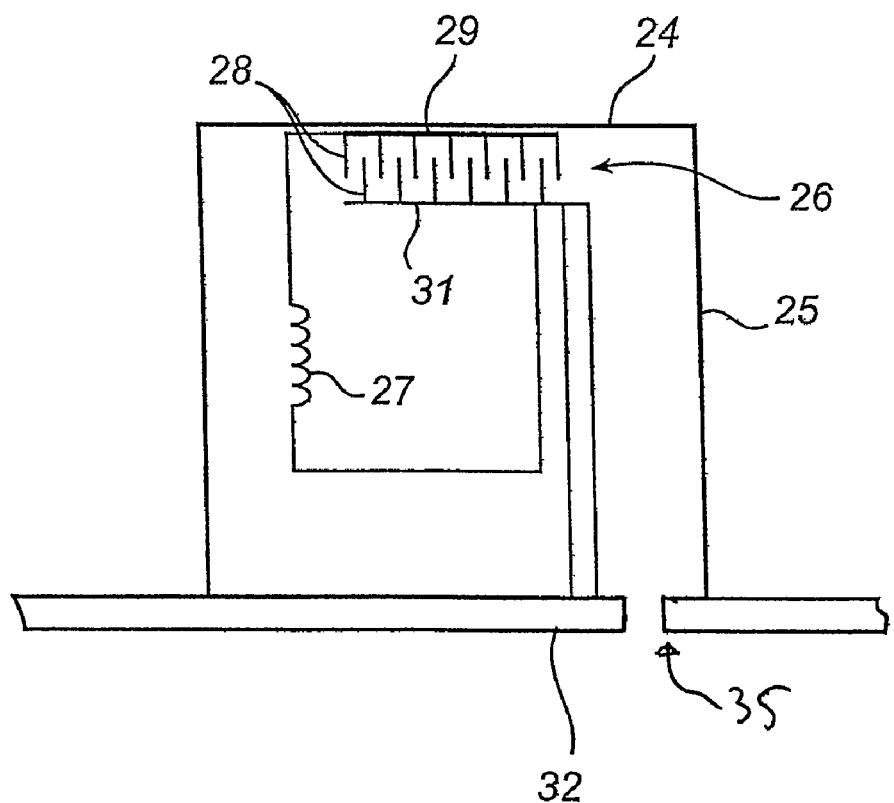
FIG. 4 shows part of FIG. 3 in larger scale.

The pressure sensor 323 comprises a container 25 with a compressible wall 24. A hole 35 in the wall 32 of the blood circuit ensures that the pressure within the container 25 is equal to atmospheric pressure. A resonance circuit is enclosed by the compressible container and comprises a variable capacitor 26 and an inductor 27. Such a sensor is shown in even larger scale in FIG. 4. The variable capacitor may have in one embodiment a number of interdigital conductors 28 in the form of fingers arranged on two opposing metal electrodes. A first of the electrodes 29 may be arranged on the compressible wall 24 while a second of the electrodes 31 may be fixed in relation to the wall 32 of the blood circuit, e.g. may be affixed to an interior wall of a tubing line 70 or a drip chamber 15. As the pressure in the extracorporeal circuit varies, the compressible wall of the container will move and accordingly the first electrode 29 and the second electrode 31 will move in relation to each other and thus the capacitance will vary. The resonance frequency of the resonance circuit constituted by the capacitor and the inductor will then vary in accordance with the capacitance of the capacitor.

Outside the blood circuit an exciter antenna 33 in FIG. 3 is arranged connected to a tunable oscillator 34 which may be controlled by a control unit 39. The oscillator may drive the antenna to influence the electromagnetic field at one or more different frequencies. In one embodiment the control unit 39 may use the grid-dip oscillator technique according to which technique the oscillator frequency is swept over the resonance frequency of the sensor, or other techniques for analyzing resonance frequencies of LC circuits. The oscillator is inductively coupled to the sensor and at the resonance frequency the sensor will be energized and thereby drain energy from the external circuit. A current-dip in the oscillator circuit may then be detected. The resonance frequency of the oscillator circuit may then be detected and may be transformed into a pressure by an established, e.g. calibrated, relationship between the frequency of the dip frequency and the fluid pressure, i.e. the difference between blood pressure and atmospheric pressure.

Figure 5A:
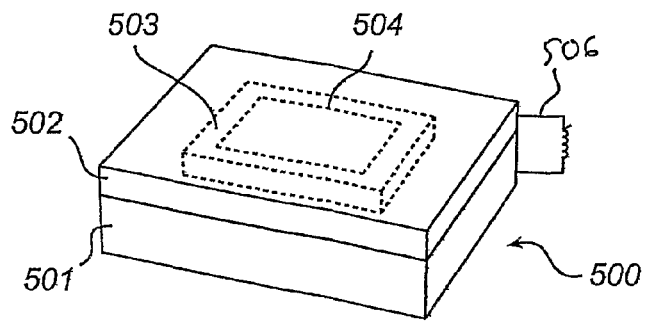
FIGS. 5a-5e show schematically a device comprising a pressure sensor.
Figure 5B:
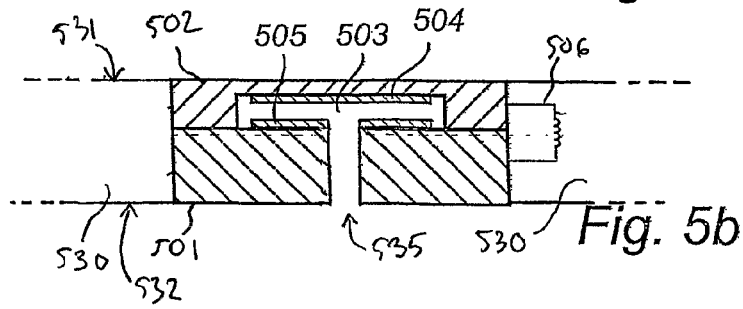

A device comprising a pressure sensor 500 will now be schematically described with reference to FIGS. 5a-d. FIG. 5a shows the sensor 500 in perspective view and FIGS. 5b-d shows the sensor 500 in cross section and forming part of a wall 530 of an extracorporeal blood circuit having an inside surface 531, being in contact with the blood, and an outside surface 532, being in contact with the outside atmosphere.

The sensor 500 comprises a substrate 501 on which a lid 502 is arranged. A cavity 503 is formed between the substrate 501 and the lid 502, whereby the substrate 501 and the lid 502 form walls of the cavity 503, defining a container. The substrate 501 and the lid 502 are made of an electrically isolating material and the cavity 503 has been formed by way of, e.g., micro machining, as is known in the art. The cavity 503 is in pressure communication with the surroundings by means of a hole 535 in the substrate 501 in the sense that exchange of gas, i.e. air, is possible between the cavity 503 and the outside of the cavity 503. The container is also compressible, where the term compressible is used in the meaning that the volume of the container may increase as well as decrease depending on the pressure in the extracorporeal circuit.

A first electrode 504 and a second electrode 505 are arranged on two opposing walls of the cavity 503 forming a capacitive arrangement. These electrodes 504, 505 form, together with an inductor 506, a resonance circuit similar to the one described above in connection with FIGS. 3 and 4.

Figure 5C:
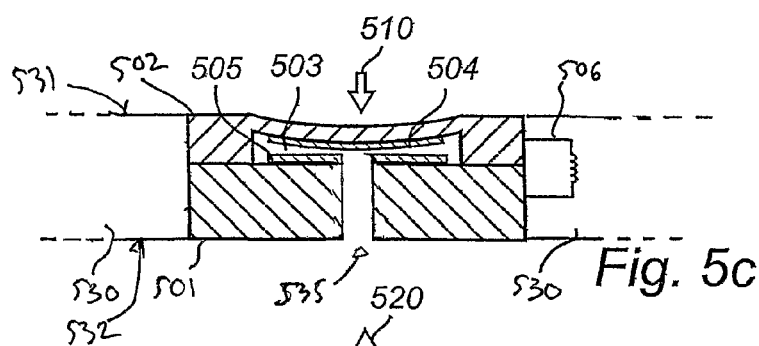
Figure 5D:
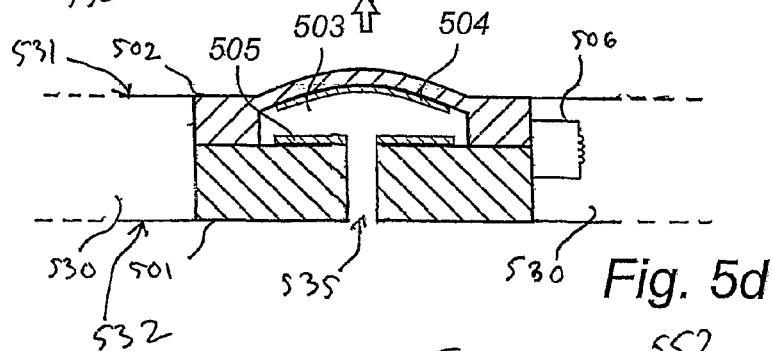

FIG. 5c illustrates a situation where the sensor 500 is located in an environment in which the pressure in the extracorporeal circuit is higher than the pressure inside the cavity 503, i.e. higher than atmospheric pressure. This leads to a net pressure force 510 acting on the lid 502 resulting in a decrease of the volume of the cavity 503. Consequently, the two electrodes 504, 505 are brought closer to each other, changing the capacitance of the electrode arrangement and thereby changing the resonance frequency of the resonance circuit.

FIG. 5d illustrates a situation where the sensor 500 is located in an environment in which the pressure in the extracorporeal circuit is lower than the pressure inside the cavity 503, i.e. lower than atmospheric pressure. This leads to a net pressure force 520 acting on the lid 502 resulting in an increase of the volume of the cavity 503. Consequently, the two electrodes 504, 505 are brought further away from each other, changing the capacitance of the electrode arrangement and thereby changing the resonance frequency of the resonance circuit.

Figure 5E:
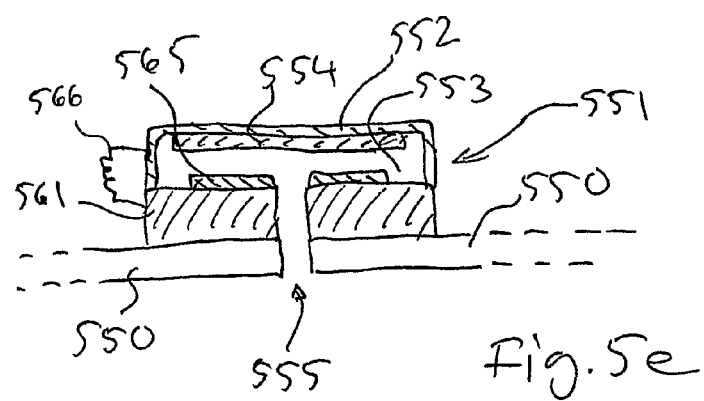

FIG. 5e illustrates schematically an alternative embodiment of a device comprising a sensor configuration. A sensor 551 is mounted, e.g. glued or welded, on the inside wall 550 of a container for a biological fluid, for example a blood container with, e.g., rigid walls. Similar to the embodiment described above, electrodes 554 and 565 and an inductor 566 are located on a sensor lid 554 and a substrate 561, respectively. A cavity 553 is formed by the lid 552 and the substrate 561. As in the previous embodiment, the cavity 553 is in pressure communication with the outside of the container for biological fluid by means of a hole 555. A pressure differences between the cavity and the inside of the container for biological fluid results in flexing of the lid 552 and consequent relative displacement of the electrodes 554 and 565.

Figure 6A:
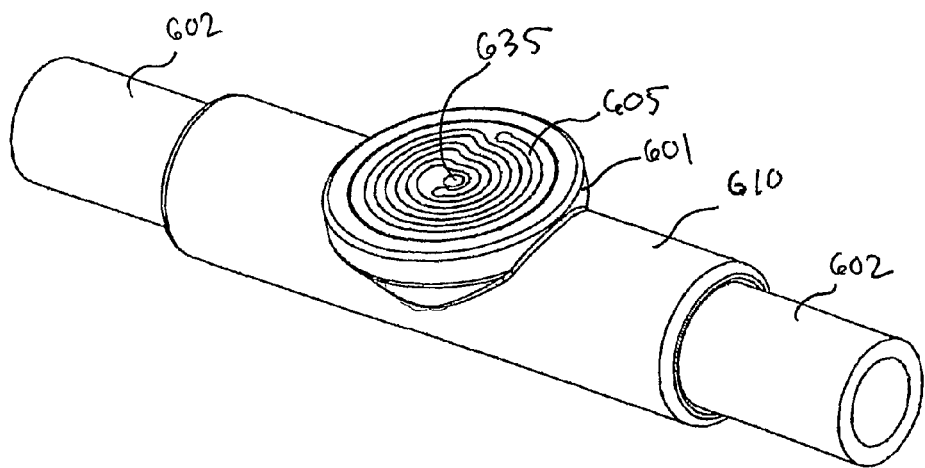
FIGS. 6a and 6b show a tube mounted pressure sensor according to an embodiment of the present invention.
Figure 6B:
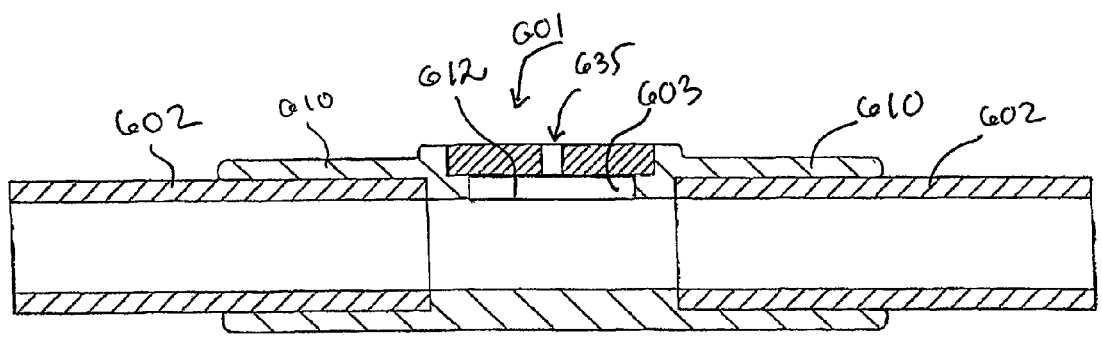

An alternative embodiment of a device according to the invention is illustrated in a perspective view in FIG. 6a and in a cross sectional view in FIG. 6b. A pressure sensor 601, similar to the sensors described above in connection with FIGS. 5a-e, comprises a cavity 603 and a hole 635 for allowing the cavity 603 to obtain atmospheric pressure. A part of an electrode pattern 605 is formed on the sensor 601. The sensor 601 is attached to a tube 602, of which only a short section is shown, by way of a housing 610. The difference between a pressure of a fluid within the tube 602 and the atmospheric pressure is sensed via a membrane 612 as described above in connection with FIGS. 5a-e.

The device, i.e. housing and sensor described above in FIGS. 6a and 6b, is manufactured, for example, by way of techniques that employ insert molding.

Figure 6C:
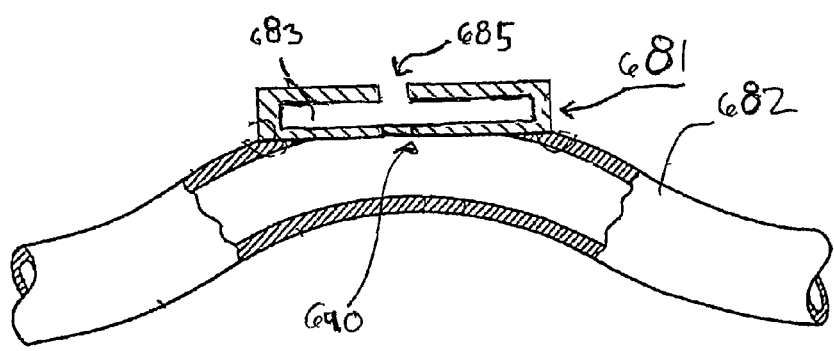
FIG. 6c shows a tube mounted pressure sensor according to an embodiment of the present invention.

Yet an alternative embodiment of a device according to the invention is illustrated in a cross sectional view in FIG. 6c. A pressure sensor 681, similar to the sensors described above in connection with FIGS. 5a-e, comprises a cavity 683 and a hole 685 for allowing the cavity 683 to obtain atmospheric pressure. A part of an electrode pattern is formed on the sensor 681. The sensor 681 is attached to a tube 682, of which only a short section is shown, at a location where the tube 682 is provided with a hole 690 as described, e.g., in the international patent application published with number WO 00/72747. The difference between a pressure of a fluid within the tube 682 and the atmospheric pressure is sensed as described above in connection with FIGS. 5a-5e.

Turning now to FIGS. 7a and 7b, a system 701 according to one embodiment of the present invention will be briefly described. The system 701 comprises a device 703, such as a cassette, which forms part of an extra-corporeal blood circuit 711, 712. Two pressure sensors 702, such as the sensors described above, are arranged in a side wall of the device 703, the arrangement being such that the sensor is mounted flush with both an inside surface and an outside surface of the wall of the device 703. It is to be noted, however, that it is not necessary that the sensor is mounted flush with the surfaces.

In operation, the device 703 is arranged at a dialysis apparatus 704, only a part of which is shown in FIGS. 7a and 7b, secured by means of mechanical coupling devices 708, 709. Within the dialysis apparatus 704 is an electromagnetic wave transmitter and a receiver located, schematically illustrated by a coil structure 705. The transmitter and receiver is controlled by a control unit (not shown) within the apparatus 704.

Figure 8A:
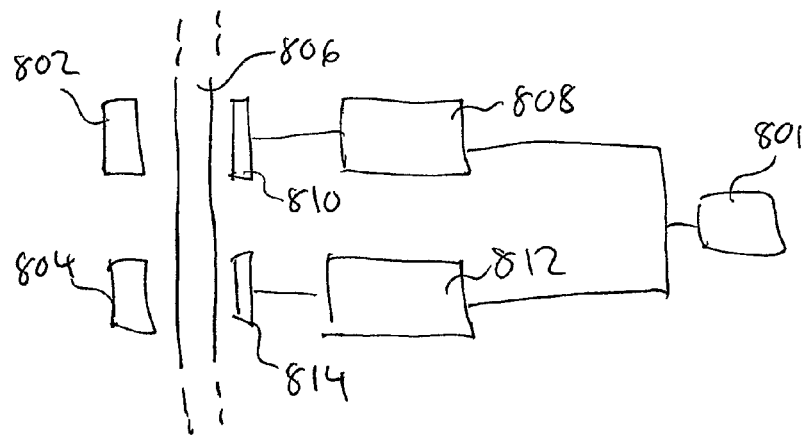
FIGS. 8a-8c show a respective system according to the present invention.
Figure 8B:
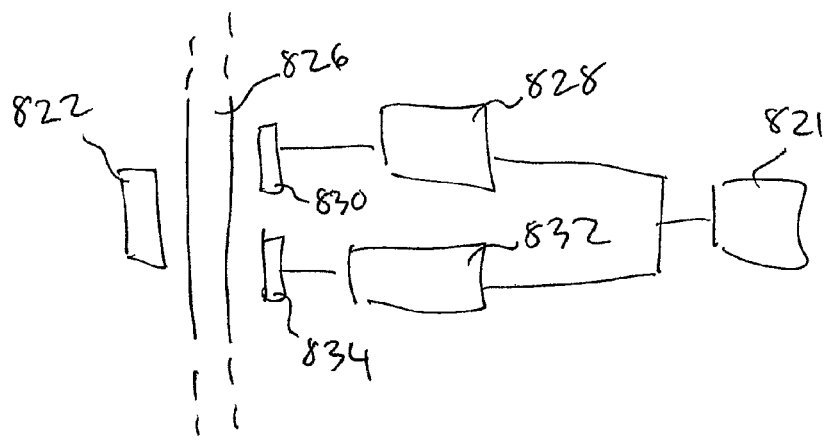
Figure 8C:
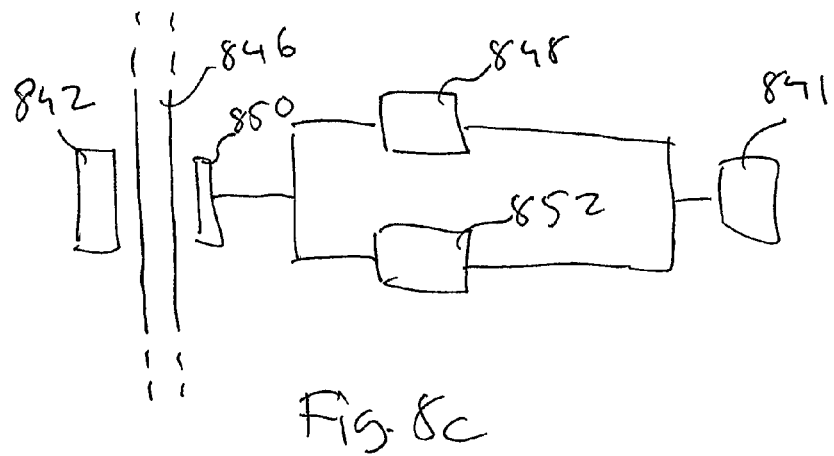

FIGS. 8a-c illustrate schematically, by way of a respective block diagram, systems according to the present invention. The systems may for example form part, as described above, of a dialysis machine of which only a respective side wall 806, 826 and 846 is illustrated. Moreover, the systems are controlled by means of a respective controller 801, 821 and 841.

In FIG. 8a, a first tunable oscillator 808 connected to a first transmitting and receiving antenna 810 communicates by way of a first alternating electromagnetic field with a first sensor 802. A second tunable oscillator 812 connected to a second transmitting and receiving antenna 814 communicates by way of a second alternating electromagnetic field with a second sensor 804. The tunable oscillators 808, 812 thereby provide a respective signal to the controller 801 indicative of the conditions sensed by the sensors 802 and 804, respectively.

In FIG. 8b, a transmitter 828 connected to a transmitting antenna 830 generates, i.e. transmits, an alternating electromagnetic field which interacts with a sensor 822. A receiver 832 receives, via a receiving antenna 834, the alternating electromagnetic field, as modified by interaction with the sensor 822, and thereby provides a signal to the controller 821 indicative of the conditions sensed by the sensor 822.

In FIG. 8c, a transmitter 848 connected to an antenna 850 generates, i.e. transmits, an alternating electromagnetic field which interacts with a sensor 842. A receiver 852 receives, via the same antenna 850, the alternating electromagnetic field, as modified by interaction with the sensor 842, and thereby provides a signal to the controller 841 indicative of the conditions sensed by the sensor 842.

After manufacture of a device comprising a pressure sensor as described above, there might be a wish to test the sensor so that one may be certain that it functions properly. One way of doing this is to apply a pressure to the sensor and measure the resonance frequency of the sensor. The sensor is made to have a certain resonance frequency without any applied pressure. If the pressure sensor has a different resonance frequency when a pressure is applied to the sensor this may be taken as an indication that the pressure sensor is functioning. However, it may be that the pressure sensor has a different resonance frequency without any applied pressure and still is non-functioning. Thus, in order to be more certain at least two different testing pressures may be applied to the sensor while the resonance frequency is measured.

The testing pressure may be applied in a number of different ways, for example as a static pressure in a pressure chamber.

By trimming during manufacturing of the pressure sensor it may be given different resonance frequencies which can thus be used to distinguish between different disposable sets. Thus, different tubing sets for use on the same machine may be identified as different tubing sets by discernment of the different resonance frequencies. Moreover, different medical procedures may also make use hereof.

As mentioned above the calibration at manufacturing and/or at the beginning of use at startup of a dialysis session can also provide for ensuring that the pressure sensor is working. This can be a function test like process to see if a proper response to the application of varying pressures by the blood pump or other mechanical alteration. The mechanical alteration may be the appliance of a mechanical force to test the electronic response frequency. The force for altering the sensor mechanically may be applied, e.g., by applying an ultrasound wave on the sensor.

The described embodiments are intended as examples only and may be modified by the man skilled in the art in a number of different ways without departing from the scope and the spirit of the invention which is defined by the appending claims.

For example the resonant sensor described above may be modified in that the inductance is made variable while the capacitance is fixed.

Another example is that the device for transporting biological fluid may be used in other extracorporeal management and/or treatments of biological fluids than specified above. Such other extracorporeal management and/or treatments may include: separation of blood into blood components; treatment to reduce pathogens such as viruses in biological fluids; absorption of specific cells or substances in blood; cell sorting and treatment of selected cells.

The invention claimed is:

1. A device for transporting biological fluid comprising:
at least one pressure sensor in fluid communication with the biological fluid, wherein the at least one pressure sensor comprises:
a container comprising at least a surface confining a cavity inside the container, said surface comprising at least one opening exposing the cavity to the atmosphere such that a reference pressure inside the cavity is equal to atmospheric pressure; and
an electric circuit arranged in the container, wherein the electric circuit is energizable by an alternating electromagnetic field at a characteristic frequency, wherein the characteristic frequency of the electric circuit is indicative of a difference between a pressure of the biological fluid and the reference pressure,
wherein the device is in at least a part of an extracorporeal circuit, said at least part of the extracorporeal circuit being disposable.

2. The device of claim 1, wherein the container is a compressible container capable of indicating pressure of the biological fluid through compression or expansion.

3. The device of claim 2, wherein the electric circuit further comprises at least one component chosen from a capacitor and an inductor, said component forming a resonance circuit energizable by the alternating electromagnetic field, wherein said characteristic frequency is a resonance frequency of the resonance circuit decided by a characteristic parameter of said component, wherein said characteristic parameter of said component is configured to vary with the compression and/or expansion of the container.

4. The device of claim 3, wherein the component is a capacitor and wherein the characteristic parameter is capacitance.

5. The device of claim 2, wherein the container includes a substantially rigid box having a membrane.

6. The device of claim 5, wherein a portion of the component is arranged on the membrane.

7. The device of claim 6, wherein the portion of the component is configured to move with a movement of the membrane.

8. The device of claim 7, wherein the portion of the component is formed from or by the membrane.

9. The device of claim 1, wherein the pressure sensor is disposed within the device.

10. The device of claim 1, wherein the characteristic frequency is a radio frequency.

11. The device of claim 1, wherein the pressure sensor is connected to the extracorporeal circuit such that it forms a portion of the circuit.

12. The device of claim 1, wherein the device is insert molded.

13. The device of claim 1, wherein the sensor is attached to a wall of the extracorporeal circuit such that a seal is formed between the sensor and the extracorporeal circuit.

14. The device of claim 1, wherein at least a part of the extracorporeal circuit is configured for at least one application chosen from dialysis, blood separation, blood donation, hemofiltration, and cardiopulmonary bypass.

15. The device of claim 1, wherein at least a part of the extracorporeal circuit is chosen from a dialyser, cassette, ultrafilter, tube, connector, container, chamber, fluid bag, blood container, collection bags, pump segment part of lineset, and oxygenator.

16. The device of claim 1, wherein the device is configured for extracorporeal biological fluid management.

17. The device of claim 16, wherein the fluid is blood.

18. The device of claim 16, wherein the management is dialysis.

19. A system for managing biological fluids, comprising:
the device of claim 1;
at least one oscillator configured to drive an antenna to provide alternating electromagnetic fields at a plurality of frequencies to the device; and
a control unit configured to detect an electrical signal from the oscillator and determine the characteristic frequency of the electric circuit in the device based on the detected electrical signal.

20. The system of claim 19, wherein the electrical signal is an current dip in the oscillator, wherein the control unit is configured to identify the frequency of the alternating electromagnetic field corresponding to the current dip as the characteristic frequency.

21. The system of claim 19, wherein the control unit is further configured to determine a pressure based on the characteristic frequency.

22. A method of pressure sensing in a biological fluid using the system of claim 19, comprising the steps of:
providing alternating electromagnetic fields at a plurality of frequencies to the device;
detecting an electrical signal from the oscillator;
determining the characteristic frequency of the electric circuit in the device based on the detected electrical signal.

23. The system of claim 22, wherein the electrical signal is an current dip in the oscillator, wherein the step of determining the characteristic frequency comprises the step of identifying the frequency of the alternating electromagnetic field corresponding to the current dip as the characteristic frequency.

24. The system of claim 22, wherein the step of determining the characteristic frequency comprises the step of determining a pressure based on the characteristic frequency.

25. The device of claim 1, wherein the container comprises at least a substrate and a lid attached to the substrate, wherein the at least one opening is located on the substrate.

26. A system for managing biological fluids, comprising:
the device of claim 1;
at least one transmitter configured to transmit a first alternating electromagnetic field to the pressure sensor in the device; and
at least one receiver configured to receive the alternating electromagnetic field as modified by its interaction with the device, wherein the received alternating electromagnetic field is indicative of a pressure sensed by the device; and
a control unit configured to control the transmitter and the receiver.

27. The system of claim 26, wherein the system forms part of a dialysis machine.

28. The system of claim 26, wherein the system is configured for extracorporeal biological fluid management.

29. The system of claim 28, wherein the fluid is blood.

30. The system of claim 28, wherein the management is dialysis.

31. A method of pressure sensing in a biological fluid using the device of claim 26, comprising the steps:
providing at least one alternating electromagnetic field to the pressure sensor;
sensing the at least one alternating electromagnetic field as modified by its interaction with the device; and
providing the sensed field as a signal that is indicative of a pressure sensed by the pressure sensor.

32. A device for transporting biological fluid, comprising:
at least one pressure sensor in fluid communication with the biological fluid configured for sensing a difference between a pressure of the biological fluid and a reference pressure, wherein the at least one pressure sensor comprises:
a container exposed to the atmosphere, such that the reference pressure within the container is equal to atmospheric pressure; and
an electric circuit within the container, wherein the electric circuit is energizable by a first alternating electromagnetic field at a characteristic frequency, wherein the characteristic frequency of the electric circuit is indicative of the difference between the pressure of the biological fluid and the reference pressure,
wherein the device is in at least a part of an extracorporeal circuit, said at least part of the extracorporeal circuit being disposable.

33. The device of claim 32, wherein the container is a compressible container capable of indicating pressure through compression or expansion.

34. The device of claim 33, wherein the electric circuit further comprises at least one component chosen from a capacitor and an inductor, said component forming a resonance circuit enerqizable by the alternating electromagnetic field, wherein said characteristic frequency is a resonance frequency of the resonance circuit decided by a characteristic parameter of said component, wherein said characteristic parameter of said component is configured to vary with the compression and/or expansion of the container.

35. The device of claim 34, wherein the component is a capacitor and wherein the characteristic parameter is capacitance.

36. The device of claim 32, wherein the characteristic frequency is a radio frequency.

37. The device of claim 32, wherein the pressure sensor is connected to the extracorporeal circuit such that it forms a portion of the circuit.

38. The device of claim 32, wherein the device is insert molded.

* * * * *